(12) United States Patent
Schleifer et al.

(10) Patent No.: US 6,242,266 B1
(45) Date of Patent: Jun. 5, 2001

(54) PREPARATION OF BIOPOLYMER ARRAYS

(75) Inventors: Arthur Schleifer, Portola Valley; Carol T. Schembri, San Mateo; Michael P. Caren, Palo Alto, all of CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 09/302,899

(22) Filed: Apr. 30, 1999

(51) Int. Cl.[7] .................. G01N 33/543; G01N 33/53; C12Q 1/68; C12P 19/34; C07H 19/00
(52) U.S. Cl. .................. 436/518; 435/6; 435/7.1; 435/91.1; 435/91.2; 435/287.2; 536/22.1; 536/23.1; 536/24.1; 536/24.31; 536/25.32
(58) Field of Search .................. 435/518, 6, 7.1, 435/91.1, 91.2, 257.2; 346/140.1, 141; 536/22.1, 23.1, 25.32, 24.1, 24.2, 24.3, 24.31, 24.32, 24.33

(56) References Cited

U.S. PATENT DOCUMENTS

| | | | |
|---|---|---|---|
| 3,974,508 | 8/1976 | Blumenthal | 346/140 R |
| 4,184,169 | 1/1980 | Taylor et al. | 346/140 R |
| 4,314,264 | 2/1982 | Bok et al. | 346/140 R |
| 4,399,446 | 8/1983 | McCann et al. | 346/140 R |
| 4,593,296 | 6/1986 | Dagna | 346/140 R |
| 4,607,261 | 8/1986 | McCann et al. | 346/75 |
| 4,679,059 | 7/1987 | Dagna | 346/140 R |
| 4,771,295 | 9/1988 | Baker et al. | 346/1.1 |
| 4,875,055 | 10/1989 | McCann et al. | 346/75 |
| 4,877,745 | 10/1989 | Hayes et al. | 436/166 |
| 4,929,969 | 5/1990 | Morris | 346/140 R |
| 4,931,811 | 6/1990 | Cowger et al. | 346/140 R |
| 5,121,132 | 6/1992 | Pan et al. | 346/1.1 |
| 5,510,817 | 4/1996 | Sohn | 347/21 |
| 5,539,952 | 7/1996 | Hayes et al. | 15/321 |
| 5,563,639 | 10/1996 | Cameron et al. | 347/34 |
| 5,658,802 | 8/1997 | Hayes et al. | 436/518 |
| 5,681,757 | 10/1997 | Hayes | 437/7 |

FOREIGN PATENT DOCUMENTS

| | | | |
|---|---|---|---|
| WO 95/25116 | 9/1995 | (WO) | C07H/21/00 |
| WO 98/10858 | 3/1998 | (WO) | B01J/19/00 |
| WO 98/25944 | 6/1998 | (WO) | C07H/21/00 |
| WO 98/41531 | 9/1998 | (WO) . | |

*Primary Examiner*—Kenneth R. Horlick
*Assistant Examiner*—Jeffrey Siew
(74) *Attorney, Agent, or Firm*—Gordon Stewart

(57) ABSTRACT

A method and apparatus for fabricating an array of biopolymers on a substrate using a biopolymer or biomonomer fluid, and using a fluid dispensing head. The head has at least one jet which can dispense droplets onto a substrate, the jet including a chamber with an orifice, and including an ejector which, when activated, causes a droplet to be ejected from the orifice. The method includes positioning the head with the orifice facing the substrate. Multiple droplets of the biopolymer or biomonomer fluid are dispensed from the head orifice so as to form an array of droplets on the substrate. A gas flow is directed through a venturi which has a throat opening communicating with the dispensing head chamber. A venturi control valve which particularly communicate with an outlet of the venturi, is adjusted to alter the chamber pressure. The venturi may be driven by a source of inert anhydrous compressed gas which assists in maintaining fluid in the head isolated from moisture.

20 Claims, 4 Drawing Sheets

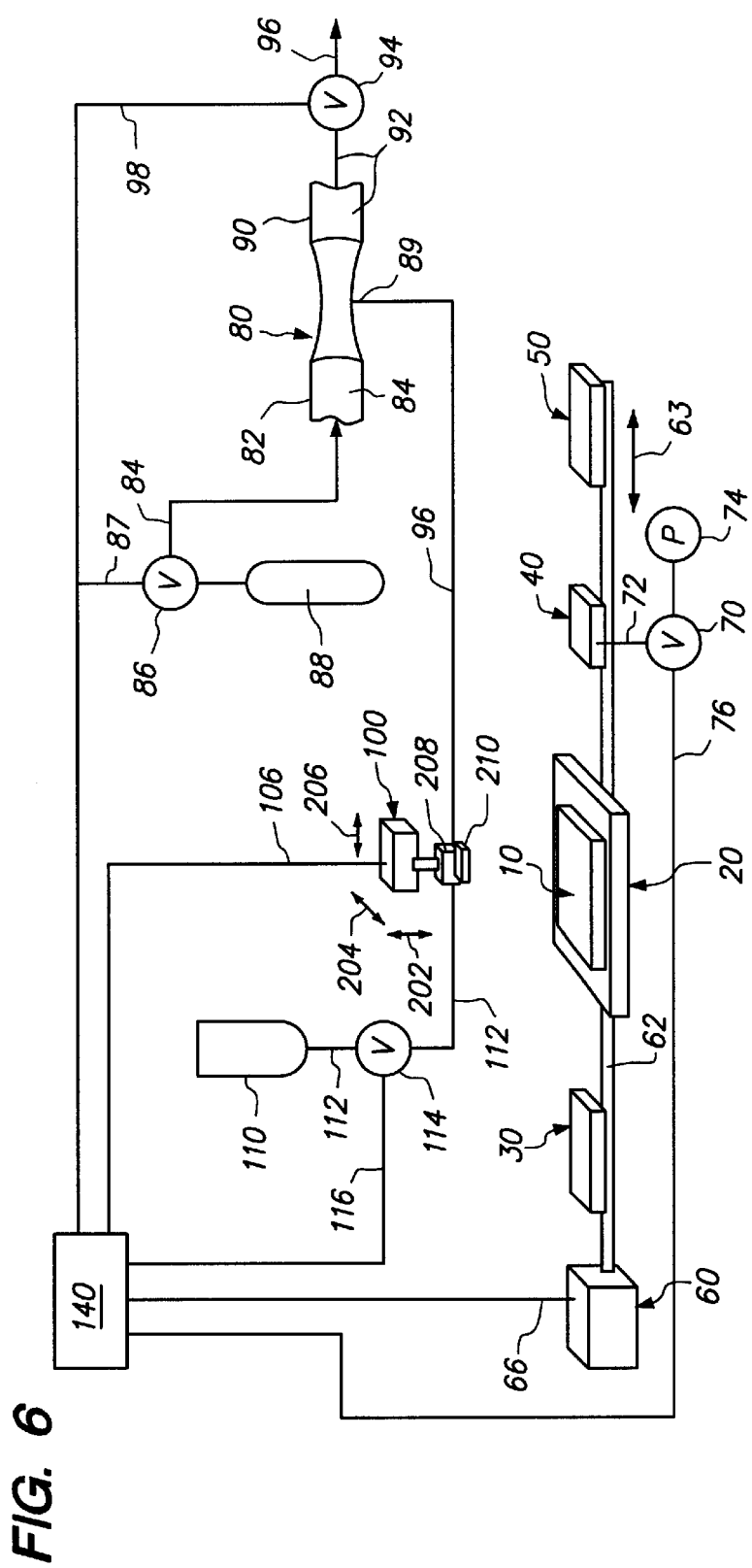
FIG. 6
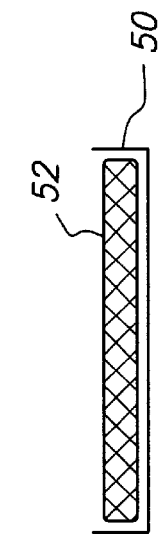
FIG. 9
FIG. 8
FIG. 7

US 6,242,266 B1

PREPARATION OF BIOPOLYMER ARRAYS

FIELD OF THE INVENTION

This invention relates to biopolymer arrays, particularly polynucleotide arrays such as DNA arrays, which are useful in diagnostic, screening, gene expression analysis, and other applications.

BACKGROUND OF THE INVENTION

Arrays of biopolymers, such as arrays of peptides or polynucleotides (such as DNA or RNA), are known and are used, for example, as diagnostic or screening tools. Such arrays include regions (sometimes referenced as spots) of usually different sequence biopolymers arranged in a predetermined configuration on a substrate. The arrays, when exposed to a sample, will exhibit a pattern of binding which is indicative of the presence and/or concentration of one or more components of the sample, such as an antigen in the case of a peptide array or a polynucleotide of particular sequence in the case of a polynucleotide array. The binding pattern can be detected, for example, by labeling all potential targets (for example, DNA) in the sample with a suitable label (such as a fluorescent compound), and accurately observing the fluorescence pattern on the array.

Biopolymer arrays can be fabricated using in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as repeating at each spot the sequence of: (a) deprotecting any previously deposited monomer so that it can now link with a subsequently deposited protected monomer; and (b) depositing a droplet of another protected monomer for linking. Different monomers may be deposited at different regions on the substrate during any one iteration so that the different regions of the completed array will have different desired biopolymer sequences. One or more intermediate further steps may be required in each iteration, such as oxidation, capping and washing steps. The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used. Reagents used in typical in situ synthesis are water sensitive, and thus the presence of moisture should be eliminated or at least minimized.

Typical procedures known in the art for deposition DNA such as whole oligomers or cDNA, are to load a small volume of DNA in solution on the tip of a pin or in an open capillary and touch the pin or capillary to the surface of the substrate. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into an inkjet head and fired onto the substrate. Such a technique has been described, for example, in PCT publications WO 95/25116 and WO 98/41531, and elsewhere. This method has the advantage of non-contact deposition. Still other methods include pipetting and positive displacement pumps such as the Bio-Dot A/D3000 Dispenser available from Bio-Dot Inc., Irvine, Calif., USA. There are four important design aspects required to fabricate an array of bioplymers such as cDNA's or DNA oligomers. First, the array sensitivity is dependent on having reproducible spots on the substrate. The location of each type of spot must be known and the spotted area should be uniformly coated with the DNA. Second, since DNA is expensive to produce, a minimum amount of the DNA solution should be loaded into any of the transfer mechanisms. Third, any cross contamination of different DNA's must be lower than the sensitivity of the final array as used in a particular assay, to prevent false positive signals. Therefore, the transfer device must be easily cleaned after each type of DNA is deposited or the device must be inexpensive enough to be a disposable. Finally, since the quantity of the assay sample is often limited, it is advantageous to make the spots small and closely spaced.

Similar technologies can be used for in-situ synthesis of biopolymer arrays, such as DNA oligomer arrays, on a solid substrate. In this case, each oligomer is formed nucleotide by nucleotide directly in the desired location on the substrate surface. This process demands repeatable drop size and accurate placement on the substrate. It is advantageous to have an easily cleaned deposition system since some of the reagents have a limited lifetime and must be purged from the system frequently. Since reagents, such as those used in conventional phosphoramidite DNA chemistry may be water sensitive, there is an additional limitation that these chemical reagents do not come in contact with water or water vapor. Therefore, the system must isolate the reagents from any air that may contain water vapor for hours to days during array fabrication. Additionally, the materials selected to construct system must be compatible with the chemical reagents thereby eliminating a lot of organic materials such as rubber.

Given the above requirements of biopolymer array fabrication, deposition using an inkjet type head is particularly favorable. In particular, inkjet deposition has advantages which include producing very small spot sizes. This allows high-density arrays to be fabricated. Furthermore, the spot size is uniform and reproducible as demonstrated by the successful use of inkjets in printers. Since it is a non-contact technique, ink-jet deposition will not scratch or damage the surface. Ink-jets have very high deposition rate, which facilitates rapid manufacture of arrays.

However, an ink-jet deposition system used for fabricating a biopolymer array, should meet a number of requirements. Specifically, the inkjet head must be capable of being loaded with very small volumes of DNA solution and function with minimal or no priming of the inkjets. The system should provide for easy purging of the working solution and readily flushed clean when required. When used for in-situ synthesis, the system should be able to to keep reagents isolated from moisture in the surrounding air. Additionally, use of an inkjet head typically requires that a negative backpressure (that is, a pressure behind an orifice of the jet), in the range of one to six inches of water, be supplied to the inkjet head so that the inkjets form repeatable droplets without dripping during times when the jet has not been activated.

Open-cell foam has been used to provide this negative backpressure in an inkjet printer in a manner disclosed in U.S. Pat. No. 4,771,295, such the capillarity of the foam creates the negative backpressure in an ink reservoir. While this is an easy and economical way to provide the required negative backpressure, the foam cannot be easily purged of the working fluid. A small rubber thimble, similar to an eyedropper, can alternatively be used but the backpressure will vary as the reservoir is depleted. In addition, rubber is incompatible with the chemical reagents typically used in in-situ synthesis. A spring bag reservoir can be designed to control the backpressure of the fluid reservoir, however it requires a large working volume and is therefore not a good choice for the small reservoir volumes required by DNA or other biopolymer array fabrication. A regulated vacuum source could also be used. However, this may permit undesirable components, such as moisture, entering the head particularly during in situ synthesis. Additionally, purging the inkjet head then requires extra valves and a compressed nitrogen (or other suitable gas) source. Gravity is one of the easiest backpressure control means, however the backpressure changes as the fluid height drops and it requires too large a fluid volume to work properly for the small volumes encountered in an inkjet. It would be desirable then, to provide an apparatus and method for fabricating arrays of biopolymers which can use an inkjet type head or other pulse jet head, and which provides for easy purging and cleaning of the head. It would further be desirable that such an apparatus and method provide a simple way of providing a controlled negative backpressure to the head and also provide a simple way of purging the head, without an overly complex system of valves. It would also be desirable that any apparatus and method facilitates isolating reagents in the head from moisture or other undesirable components, and that it is of a compact construction given the small size of other components typically encountered in polynucleotide synthesis.

SUMMARY OF THE INVENTION

The present invention then, provides a method of fabricating an array of different or the same moieties (for example, multiple different chemical compounds) on a substrate using one or more suitable fluids, and using a fluid dispensing head. The invention is particularly useful for the in situ process since it provides the required head pressure while facilitating isolation of reagents from moisture or other undesirable components. However, the invention is also applicable to the direct deposition of polynucleotides. Particularly, the invention provides a method of fabricating an array of biopolymers using a biopolymer containing fluid, or one or more fluids containing a biomonomer. The head has at least one jet which can dispense droplets of a fluid onto a substrate, the jet including a chamber with an orifice, and including an ejector which, when activated, causes a droplet to be ejected from the orifice. The head may particularly be of a type commonly used in inkjet printers, in which a plurality of pulse jets (such as those with thermal or piezoelectric ejectors) are used, with their orifices on a common front surface of the head.

The method comprises positioning the head with the orifice facing the substrate. Multiple fluid droplets of the biopolymer, biomonomer or other fluid, are dispensed from the head orifice so as to form an array of droplets on the substrate (this formed array may or may not be the same as the final desired array since, for example, multiple heads can be used to form the final array). A gas flow is directed through a venturi which has a throat opening communicating with the dispensing head chamber. The gas used may be any suitable gas which may be selected depending upon the reagent chemistry. For example, when phosphoramidite oligonucleotide synthesis or other water sensitive chemistries are used, the gas should preferably be an inert anhydrous compressed gas such as anhydrous nitrogen. By "inert" in this context is referenced no substantial adverse reaction with a reagent. Gas flow rate through the venturi may be adjusted to alter the chamber pressure. This adjustment can occur whenever it is desired to change the pressure in the chamber, for example before or after the dispensing step. The adjustment can be accomplished by suitable means such as a valve on the venturi inlet and/or outlet side, or some other way of at least partially obstructing the inlet and/or outlet side (for example, an operator may simply manually block the outlet side). It will be appreciated from this arrangement, that all of the pressures in or at various chambers in the head therefore, are typically gas pressure (that is, provided by a gas in the location specified).

The venturi throat opening may provide a negative spotting pressure to the head chamber during dispensing of the droplets, and the gas flow resistance of the venturi outlet side may be adjusted (before or after dispensing) to provide a positive chamber pressure. This positive pressure may be provided by increasing the gas flow resistance of the venturi outlet side before dispensing (for example, as a priming pressure so as to assist in priming the jets) or after dispensing (for example, as a purging pressure so as to assist in purging any fluid remaining in the chamber out through the orifice). The priming and purging pressures may be the same or different, and each will typically be higher than the spotting pressure. In the case of purging, a purge fluid may optionally be added to the head chamber prior to providing the purging pressure.

In one aspect of the method, which is particularly useful for (but not limited to) the in situ method, the chamber is loaded with the fluid from a direction behind the orifice (that is, liquid is not loaded through the orifice). Following loading, the gas flow resistance of the venturi outlet side is increased to provide a positive priming pressure to the chamber. This assists in forcing liquid into the one or more jets to prime them.

In another aspect, which is particularly useful for (but not limited to) the deposition of previously obtained biopolymers, the method may additionally include, prior to the dispensing step, loading the head with a fluid, such as a fluid containing a biomonomer (for example, a nucleotide reagent), biopolymer (for example, a pre-synthesized oligonucleotide, cDNA, or DNA purified or amplified from a natural source), or other fluid (for example a fluid containing a moiety or a reagent used in producing such chemical a moiety). This loading step includes positioning the head facing a load station which is spaced from the substrate, with the one or more orifices adjacent and facing the fluid to be loaded. A loading pressure is provided in the chamber from the venturi throat opening while the head is facing the load station, which is sufficiently negative such that the fluid is drawn into the chamber through the one or more orifices. The gas flow rate through the venturi is adjusted to provide a spotting pressure to the chamber while dispensing droplets from the head, which spotting pressure may be the same or higher (that is, less negative) than the loading pressure. This adjustment may, for example, be accomplished by adjusting a valve on the inlet side of the venturi.

The method may include the loading, spotting and purging steps as described above.

In another aspect, the present invention provides a method of fabricating an array of different moieties, particularly biopolymers on a substrate using a biopolymer or biomonomer fluid, and using a fluid dispensing head as described above, which method includes positioning the head with the orifice facing the substrate. Multiple fluid droplets of the biopolymer, biomonomer, or other fluid are dispensed from the head so as to form an array of droplets on the substrate. A flow of inert anhydrous gas is directed through a venturi which has a throat opening communicating with the dispensing head chamber. This aspect may additionally include providing any of the loading, spotting and purging pressures, in the same manners as mentioned above. The head used in the method may have multiple pulse jets with orifices on a common front face of the head, such as a typical inkjet printing head. In this case, some or all of the jets can be loaded with the same or different fluids (biopolymer or otherwise, for example, deprotection reagent or other reagent).

An apparatus which can be used to execute a method of the present invention is also provided. In one aspect, the apparatus comprises a substrate station on which the substrate can be mounted, and a fluid dispensing head, and venturi, all as described above. The apparatus may further include a source of inert anhydrous gas communicating with the venturi pressurized inlet, and/or a valve to adjust the gas flow rate through the venturi (the valve being on the inlet or outlet side of the venturi, or a valve can be provided on both sides). A positioning system moves at least one of the dispensing head and mounted substrate with respect to the other, so that multiple droplets dispensed from the head onto the substrate will form an array thereon. The apparatus may further include, particularly in the aspect used for deposition of previously obtained biopolymers, the load and purge stations. A control processor may be present to operate the positioning system to selectively position the head facing any one of the stations, and which processor also adjusts the venturi outlet control valve to any of the required positions. In a particular embodiment, the load station comprises a plate on which multiple drops of different solutions can be retained.

The method and apparatus of the present invention can provide a simple way of controlling backpressure in a pulse type fluid dispensing head, and can also provide a simple way of purging the head, without requiring an overly complex system of valves. The apparatus and method can also facilitate isolating reagents in the head from moisture or other undesirable components.

BRIEF DESCRIPTION OF THE DRAWINGS

FIG. 6 is another embodiment of an apparatus of the present invention;

FIG. 7 is an enlarged cross-section of a load station of the apparatus of FIG. 1;

FIG. 8 is an enlarged cross-section of a purge station of the apparatus of FIG. 1;

FIG. 9 is an enlarged cross-section of a cleaning station of the apparatus of FIG. 1;

To facilitate understanding, identical reference numerals have been used, where practical, to designate corresponding elements that are common to the Figures. Figure components are not drawn to scale.

DETAILED DESCRIPTION OF EMBODIMENTS OF THE INVENTION

In the present application, unless a contrary intention appears, the following terms refer to the indicated characteristics. A "biopolymer" includes peptides or polynucleotides, as well as such compounds composed of or containing amino acid or nucleotide analogs or non-nucleotide groups. This includes those compounds in which the conventional polynucleotide backbone has been replaced with a non-naturally occurring or synthetic backbone, and those a nucleic acid in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. A "nucleotide" refers to a subunit of a nucleic acid and includes a phosphate group, a 5 carbon sugar and a nitrogen containing base, as well as analogs of such subunits. Specifically, a "biopolymer" includes DNA (including cDNA), RNA and oligonucleotides. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a fluid containing either a biomonomer or biopolymer, respectively. An "array", unless a contrary intention appears, includes any one or two dimensional arrangement of discrete regions bearing particular moieties (for example, different polynucleotide sequences) associated with that region. It will also be appreciated that throughout the present application, words such as "upper", "lower" and the like are used with reference to a particular orientation of the apparatus with respect to gravity, but it will be understood that other operating orientations of the apparatus or any of its components, with respect to gravity, are possible. Reference to a "droplet" being dispensed from a pulse jet herein, merely refers to a discrete small quantity of fluid (usually less than about 1000 pL) being dispensed upon a single pulse of the pulse jet (corresponding to a single activation of an ejector) and does not require any particular shape of this discrete quantity. "Fluid" is used herein to reference a liquid. Further, when reference is made in this application to providing a pressure within the dispensing head or a chamber therein this refers, unless a contrary indication appears, to a pressure therein relative to the pressure immediately outside the head pulse jet orifices. Such pressures can be provided by varying the pressure outside the head, or inside the head, or both.

Figure 1:
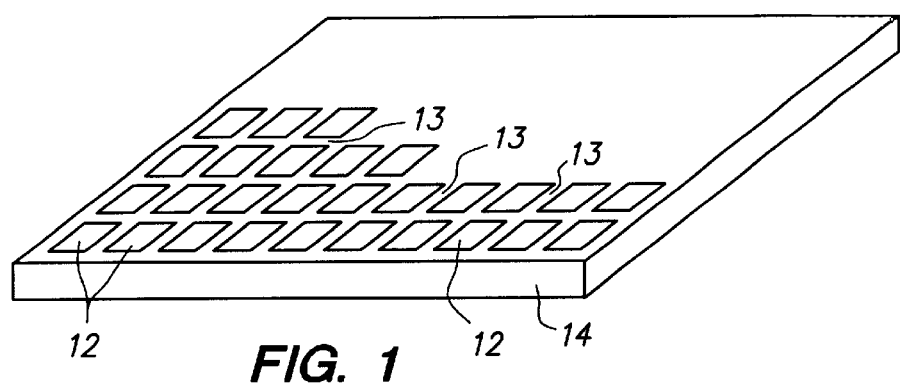
FIG. 1 is a perspective view of a substrate bearing multiple arrays, as may be produced by a method and apparatus of the present invention.

Referring first to FIG. 1, either embodiment of invention described below may produce multiple identical arrays 12 (only some of which are shown in FIG. 1) across the complete surface of a single substrate 14. However, the arrays 12 produced on a given substrate need not be identical and some or all could be different. Each array 12 will contain multiple spots or regions, 16. As mentioned above, an array 12 may contain any number of multiple regions, with a typical number being from 100 to 10,000 regions (although more or less are possible). All of the regions 16 may be different, or some or all could be the same. All of the regions 16 may be different, or some or all could be the same. Each region carries a predetermined moiety or a predetermined mixture of moieties, such as a particular polynucleotide sequence or a predetermined mixture of polynucleotides. This is illustrated somewhat schematically in FIG. 3 where regions 16 are shown as carrying different polynucleotide sequences.

Figure 4:
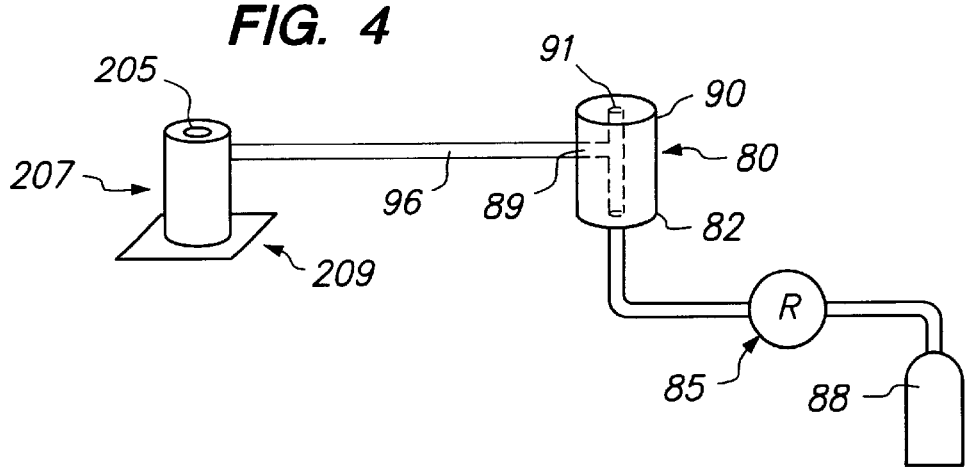
FIG. 4 is a schematic view showing components of an apparatus of the present invention.

Referring to FIG. 4 the illustrated apparatus includes a fluid dispensing head 209 which is positioned on a reagent reservoir 207. Head 209 is an inkjet type of printing head with multiple jets each having an orifice, a dispensing chamber and an ejector which, when activated, causes a droplet to be ejected from the orifice. Head 209 may be of similar construction to head 210 described below in connection with FIGS. 6 and 10–12. However, cover 219 and the individual reservoir chambers 222 of head 210 may be omitted. Each reservoir 207 may have a capacity of only about 1 or 2 ml. A septum 205 allows sealed access to the interior chamber defined by reservoir 207 by means of a syringe. Septum 205 may be made of rubber or other suitable resilient material in a known manner. A venturi 80 has inlet and outlet sides 82, 90, respectively, an outlet opening 91, and a throat opening which communicates with reservoir 207 and hence communicates with the dispensing chambers of head 209. A flow of an anhydrous inert gas (particularly nitrogen) can be directed through venturi 80 from an adjustable flow regulator 85 (which may be regarded as a type of valve) and compressed nitrogen tank 88.

Figure 5:
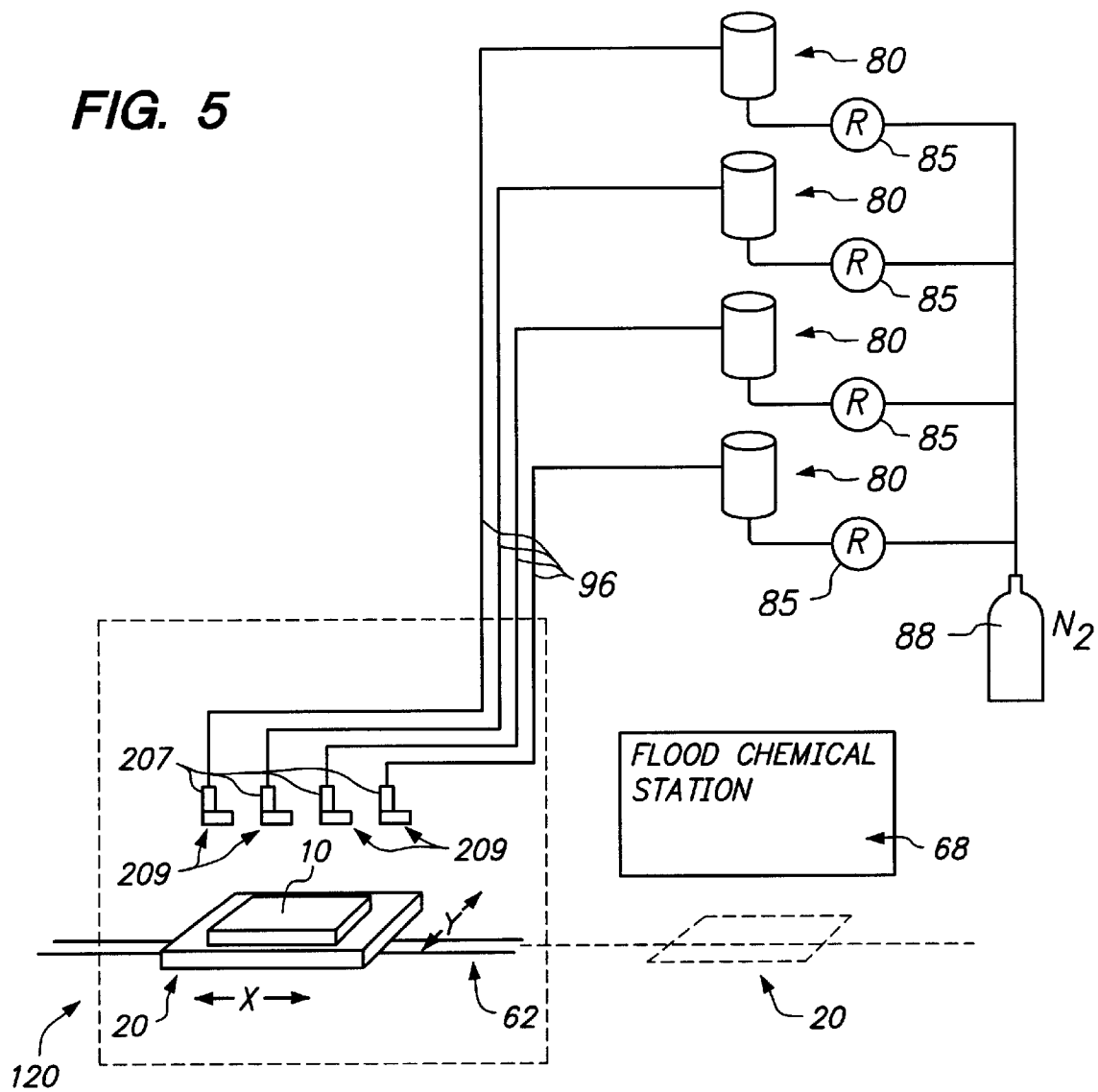
FIG. 5 is a schematic view of an apparatus of the present invention utilizing the components of FIG. 4.

An apparatus using the components of FIG. 4 is schematically illustrated in FIG. 5. This apparatus is particularly useful for an in situ method of forming polynucleotides on a substrate 10 using a procedure such as mentioned above. Four sets of the components shown in FIG. 4 are used in the apparatus of FIG. 5, with the exception that only a single compressed nitrogen tank 88 is used to supply all four adjustable flow regulators 85. A substrate station 20 can receive and retain substrate 10 thereon. A flood station 68 is provided to expose an entire substrate with reagents which are used in the in situ process to simultaneously treat all regions 16 during their formation (for example, with deprotection and washing solutions). Substrate station 20 is mounted for movement on a carriage 62 in both an "X" and "Y" direction using a suitable transporter (not shown). An enclosure 120 is positioned about the dispensing heads 209 and arranged to allow substrate station 20 to move in and out of it. Enclosure 120 permits the head and substrate station to be maintained in a controlled atmosphere environment (such as an anhydrous nitrogen atmosphere provided from a suitable external source). Movement of substrate station 20 and operation of heads 209 and flood station 68, can all be coordinated by a suitable processor in an analogous manner to that described in connection with the embodiment FIG. 6.

In operation of the apparatus of FIG. 5, flow regulators 85 can be manually adjusted to direct an anhydrous nitrogen flow through each venturi 80 from the inlet side 82 to the outlet side 90. The flow rate is sufficient to provide the spotting pressure to each of the four reservoirs 207. Suitable spotting pressures (which will be slightly negative) are mentioned below. In the event that any water vapor may be present in reservoirs 207, they can initially be flushed with anhydrous nitrogen by increasing gas flow resistance on the outlet side 90 of each venturi. This can be accomplished such as by briefly manually blocking each outlet opening 91 (an operator can readily use their finger for this purpose since each venturi 80 may only be in the order of less than 10 mm in width or length). Alternatively, a valve (such as valve 94 described in connection with FIG. 6) communicating with outlet side 90, could be used rather than manual blocking. This causes a nitrogen flow from regulators 85 to be briefly forced through lines 96 and hence into reservoirs 207 and out the orifices of the heads 209. Following flushing, the pressure within reservoirs 207 returns to the spotting pressure. Each of reservoirs 207 may then be loaded with respective nucleotide reagents through its septum 205 using a syringe. Given the capillary size of the dispensing chambers and orifices of heads 209, all jets may not be properly primed such that activation of any ejector may not yield a droplet of the expected volume. To ensure proper priming, a priming pressure (which is a positive pressure) can be applied to reservoirs 207. This can be accomplished by again increasing gas flow resistance on the outlet side 90 of venturis 80, in a manner already described. Enclosure 120 is provided with a nitrogen atmosphere and carriage 62 positions substrate 10 within enclosure 120 facing the orifices of heads 209. The processor then controls movement of substrate 10 in the X and Y directions while co-ordinating activation of the ejectors in heads 209, such that droplets are dispensed from heads 209 so as to form an initial array or pattern of droplets on substrate 10. A single array or multiple arrays of droplets can be dispensed in this manner with intervening movement of substrate 10 by carriage 62 to flood station 68 for treatment of all deposited spots with reagents, as required. The final product is one or more biopolymer arrays on substrate 10.

Typically, there is sufficient capacity within reservoirs 207 such that many substrates 10 can be treated in turn by the above method to form many arrays. At some point though, it becomes necessary to flush reservoirs 207 and heads 209. Gas flow resistance on the outlet side 90 of each venturi can then be increased in a manner already described. As already mentioned, this will cause nitrogen to flow through lines 96 and increase pressure within reservoirs 207 to what is referenced as a "purging pressure", so as to force any liquid within reservoirs 207 out through the orifices in heads 209. This purging pressure is, in practice, a positive pressure which may be about the same as the priming pressure. Openings 91 can be uncovered when all liquid appears to have been purged from reservoirs 207. A syringe can then be used to add a purge fluid (such as a solvent) to each reservoir 207 through septa 205, and the foregoing purging procedure repeated.

Referring now to the embodiment of FIG. 6 the apparatus includes a substrate station 20 on which can be mounted the substrate 14. Substrate station 20 can include a vacuum chuck connected to a suitable vacuum source (not shown) to retain a mounted substrate 14 without exerting too much pressure thereon, since substrate 14 is often made of glass. A load station 30, purge station 40, and cleaning station 50 are spaced apart from one another an substrate station 20. Load station 30 can be of any construction with regions which can retain small volumes of different fluids for loading into head 210. For example, it may be a glass surface with different hydrophobic and hydrophilic regions to retain different drops thereon in the hydrophilic regions. Alternatively, the flexible microtitre plate described in U.S. patent application "Method and Apparatus for Liquid Transfer", Ser. No. 09/183,604 could be used. In the drawings load station 30 and has an upper surface with small notches 32 to assist in retaining multiple individual drops of a biomonomer or biopolymer fluid on that surface. The number of notches 32 or other regions for retaining drops of different fluids, is at least equal to (and can be greater than) the number of reservoir chambers 222 in a printer head 210 (described further below), and are spaced to align with orifices 214 in head 210. Even where the number of such fluid retaining regions is less than the number of orifices 214, all delivery chambers communicating with one another (through a reservoir chamber 222) can still be filled in the present invention. This occurs since, with the previously defined load pressure value, fluid which has entered a reservoir chamber 222 through one orifice 214 can still be drawn by capillary pressure into other delivery chambers communicating with the same reservoir chamber 222.

Purge station 40 has an upper surface defined by a generally rectangular urethane gasket 43 and a region 42 interior of gasket 43. Interior region 42 communicates with a vacuum line 72. A vacuum source 74 communicates through vacuum line 72 and an electrically controlled valve 70, which is controlled by a processor 140 through control line 76. Vacuum source may include a suitable vacuum supply (such as a pump) as well as a trap. Gasket 43 is dimensioned such that a periphery of a front face of a dispensing head 210 (described in more detail below) can sealingly engage against upper surface 43 with interior region 42 aligned and communicating with the two rows of orifices 214 in head 210. In this manner, orifices 214 can be placed in communication with vacuum line 72 so that, during a purging step (described further below) vacuum from line 72 can pull fluid out of head 210 through orifices 214. Any processor in the present application, including processor 140, may be a general purpose microprocessor suitably programmed to execute all of the steps required by the present invention, or any hardware or software combination which will perform the required functions.

Cleaning station 50 can retain an upwardly facing pad 52 which can be saturated with a suitable cleaning fluid. A dispensing head 210 (described in more detail below) is retained by a head retainer 208. Head 210 can be positioned to face any one of loading station 30, substrate station 20, purge station 40, or cleaning station 50 by a positioning system. The positioning system includes a carriage 62 connected to each of the foregoing stations, a transporter 60 controlled by processor 140 through line 66, and a second transporter 100 controlled by processor 140 through line 106. Transporter 60 and carriage 62 are used execute one axis positioning of any of the stations 20, 30, 40 and 50 facing the dispensing head 210 by moving them in the direction of arrow 63, while transporter 100 is used to provide two axis adjustment of the position of head 210 in a vertical direction 202 or in the direction 204. Further, once substrate station 20 has been positioned facing head 210, transporter 100 will be used to scan head 208 across a mounted substrate 10, line by line. However, it will be appreciated that both transporters 60 and 100, or either one of them, with suitable construction, can be used to perform any necessary positioning (including the foregoing scanning) of head 210 with respect to any of the stations. Thus, when the present application recites "positioning" one element (such as head 210) in relation to another element (such as one of the stations 20, 30, 40 or 50) it will be understood that any required moving can be accomplished by moving either element or a combination of both of them.

Head retainer 208, and hence head 210 (specifically, delivery chambers 217 of head 210 as described below), communicates with a source of purging fluid, such as tank 110, through line 112 in which is provided an electrically operable valve 114 controlled by processor 140 through control line 116. The apparatus further includes a venturi 80 having an inlet side 82 communicating through line 84 and an adjustable flow regulator 86, with a source of compressed anhydrous inert gas in the form of nitrogen tank 88. Flow regulator may optionally be adjusted under control of processor 140 through line 87. Since a flow regulator may be regarded as a type of valve, flow regulator 86 will often be referenced herein as valve 86. An adjustable venturi outlet control valve 94 communicates with a venturi outlet 90 through line 92. Valve 94 is electrically operable by processor 140 through line 98 and may be of any suitable type, such a simple pivoting gate valve. A throat opening 89 in venturi 80 communicates with head retainer 208, and hence head 210, through line 96. It will be appreciated that with the foregoing arrangement, selectable negative or positive pressure can be applied to head 210 from throat opening 89 by adjustment of valve 94 only. Optionally, selectable negative pressures can also be applied by adjustment of valve 86. Thus, in the discussion below where negative pressures are varied by adjusting valve 94, it will be understood that this can instead (or additionally) be accomplished by adjusting valve 86, and that corresponding settings of valve 86 (or both valves) for providing the recited negative pressures can be substituted for the negative pressure producing settings of valve 94. Furthermore, it will be appreciated that when valve 94 is at least partially closed to provide a positive pressure in head 210 from throat opening 89, such pressure will be provided by the anhydrous nitrogen from cylinder 88 thereby avoiding contact of fluid in head 210 with moisture or other contaminants. However, if the fluids in head are not sensitive to moisture or other particular gasses, a source of compressed gas other than the anhydrous nitrogen source can be used. When the fluids are moisture or otherwise sensitive, dispensing station 20 and head 208, and such other components as may be required or desired, can be enclosed in a controlled atmosphere environment (such as a nitrogen fed environment).

Figure 10:
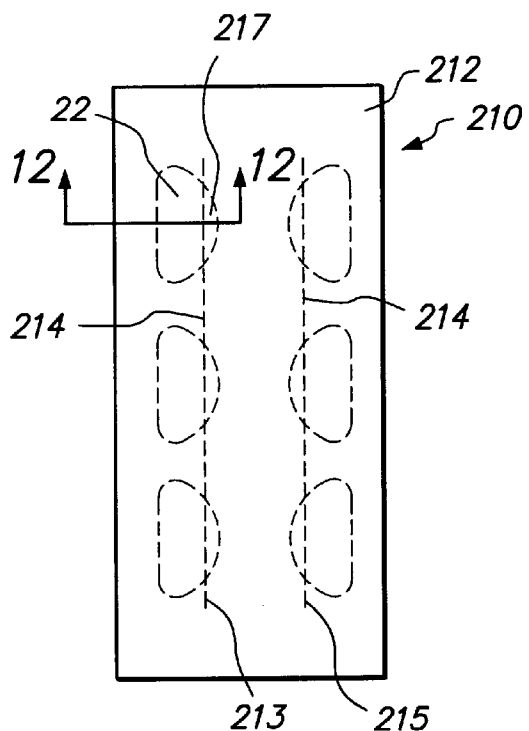
FIG. 10 is a top view of a fluid dispensing head used in an apparatus of the present invention.
Figure 11:
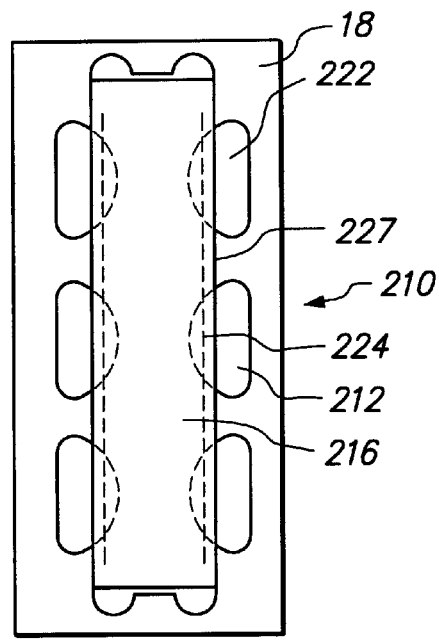
FIG. 11 is a bottom view of the head of FIG. 10.

Referring now to Figures FIGS. 10, 11, these show in plan view a particular fluid dispensing head 210 of the apparatus of FIG. 6. Head 210 has multiple fluid dispensing jets, and six reservoir chambers 222 and three hundred capillary delivery chambers 217. In a front view, FIG. 10, an orifice member 212 (here an orifice plate) represents a front face of head 210, and has orifices 214 disposed in two orifice rows 213, 215. Each orifice 214 can be regarded as part of a delivery chamber 217, and tapers inwardly away from a delivery chamber 217 toward an open end 214a of the orifice 214. Prototypes having this configuration were constructed having 150 orifices in each of the orifice rows. Thus, while each fluid pulse jet includes a fluid dispensing chamber 217, an ejector 224 as described below, and a reservoir chamber 222, the six reservoir chambers 222 are shared among a number of delivery chambers 217 (that is, each reservoir chamber 222 has multiple delivery chambers 217), while each pulse jet, of course, has its own ejector 224. It will be appreciated that the number of orifices and corresponding ejectors could of course be varied, for example between 10 to 300 or to 500 or more, depending upon their size and materials used to construct head 210. Rearward of orifice member 212 are barrier 220 and adhesive 221, and, resting upon adhesive 221 is reservoir block 218 and resting upon barrier 220 is back member 216 (here a silicon die, as described more fully below), all more readily understood with reference to a rear view as in FIG. 11 and to a sectional view as in FIG. 12.

In a particular configuration, the barrier 220 is a photo polymer layer, and accordingly the delivery chambers (for example delivery chambers 217) are defined in part by the inner surface 211 of the orifice plate 212, in part by the front surface of the margin (for example surface 226) of the back member 216, and in part by an edge (for example edge 225) of the portion of the photo polymer layer 220 situated between the orifice plate and the back member. And, in such a configuration, the reservoirs (for example reservoir 222), which are not separate from the delivery chambers, are defined in part by a portion of an edge of the back member (for example edge portion 227), and in part by an inner wall (for example wall 228) of the reservoir block 218 together with an edge (for example edge 229) of the adhesive layer, situated partly between the reservoir block 218 and the orifice plate 212.

A cover 219 (removed in FIG. 11; shown in sectional view in FIG. 12) is affixed to the rear surface of the reservoir block 218, and sealed peripherally (for example by means of an "O" ring 223) so that it provides a common enclosure for the reservoirs. Cover 219 is provided with a port 221, permits communication with holder 208 and hence lines 112 and 97. As will be appreciated, the delivery chambers and reservoirs of the device of FIGS. 10–12 can be filled with fluid by contacting the exit ends of the orifices with a quantity of the fluid and then lowering the pressure upstream from the orifices by connecting a source of vacuum at the port in the cover, resulting in drawing fluid in an upstream direction through the orifices into the delivery chambers and then into the reservoirs. Selected different fluids (or fluids containing different materials) can be drawn into the different chambers and reservoirs by contacting each orifice group (in fluid communication with a delivery chamber) with a different fluid.

Opposite each orifice 214 on the front surface 226 of the margin of the back member is an ejector 224 (here an electrical resistor operating as a heating element), which is electrically connected to a source of electrical energy which can be controlled to deliver a suitable pulse of electricity to activate the ejector on demand. (The connectors, the source of electrical energy, and the controller are not shown in the Figs.). In a particular embodiment the back member is a silicon die, and the electrical parts (heating element and connectors, for example) are formed using conventional solid state silicon ship manufacturing techniques.

The various fluid-handling parts of the head 210 generally have the following characteristics. The size of each orifice in the orifice plate is one that produces a spot of suitable dimensions on the substrate surface, where the orifice generally has an exit diameter (or exit diagonal depending upon the particular format of the device) in the range about 1 $\mu$m to 1 mm, usually about 5 $\mu$m to 100 $\mu$m, and more usually about 10 $\mu$m to 60 $\mu$m. The fluid capacity of the delivery chamber is in the range about 1 pL to 10 nL, usually about 10 pL to 5 nL and more usually about 50 pL to 1.5 nL. The reservoir chamber 222 and the connected delivery chamber 217, with which any one of the orifices 214 communicate, together have a combined fluid capacity in the range about 1 pL up to 1 mL (more typically less than 100 $\mu$L), usually about 0.5 $\mu$L to 10 $\mu$L, and more usually about 1 $\mu$L to 5 $\mu$L. The front-to-rear thickness of the delivery chamber, defined by the space between the rear surface of the orifice plate and the front surface of the margin of the back plate, may in some embodiments be in the range less than about 100 $\mu$m, for example in prototypes of embodiments shown in the Figures herein, in the range 10 $\mu$m to 60 $\mu$m.

Where the ejector is a heating element, the heating element will preferably be made out of a material that can deliver a quick energy pulse, and suitable materials include TaAl and the like. The thermal element is capable of achieving temperatures sufficient to vaporize a sufficient volume of the fluid in the firing chamber to produce a bubble of suitable dimensions upon actuation of the ejector. Generally, the heating element is capable of attaining temperatures at least about 100° C., usually at least about 400° C., and more usually at least about 700° C., and the temperature achievable by the heating element may be as high as 1000° C. or higher. It will be appreciated of course, that other ejector types, such as piezoelectric ejectors, could be used instead of a heating element.

Figure 12:
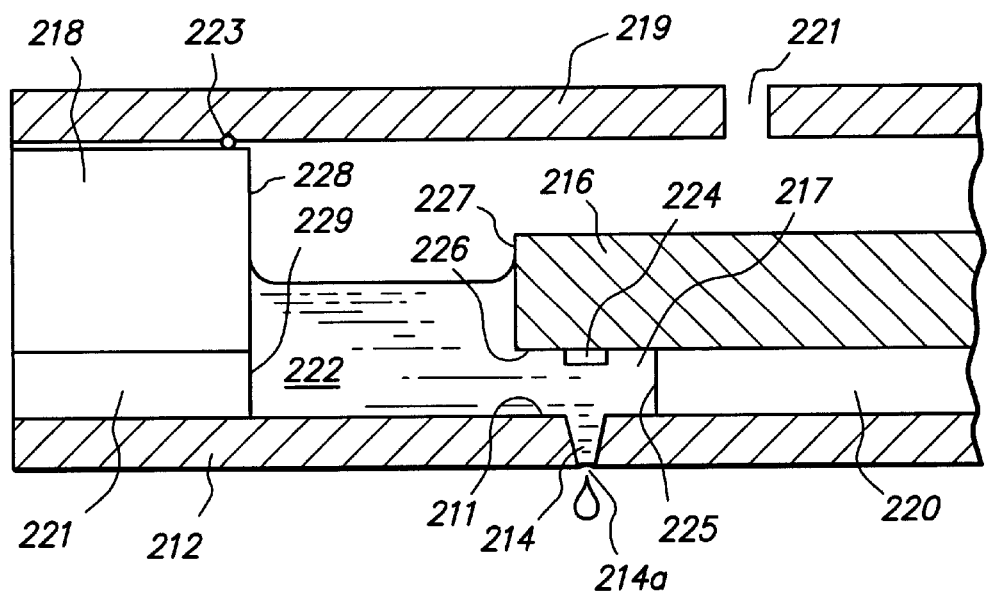
FIG. 12 is a cross-section along the line 12—12 in FIG. 10.

A device as in FIGS. 10–12 can be constructed by adaptation of techniques known in the printing art and, particularly, in the art of inkjet device construction. Certain elements of the device of FIGS. 10–12 can be adapted from parts of a commercially available thermal inkjet print head device available from Hewlett-Packard Co. as part no. HP51645A. Various other dispensing head designs can be used, such as those described in U.S. patent application entitled "A MULTIPLE RESERVOIR INK JET DEVICE FOR THE FABRICATION OF BIOMOLECULAR ARRAYS" Ser. No. 09/150,507 filed Sep. 9, 1998. That reference and all other references cited in the present application are incorporated herein by reference.

It should be noted that the above dimensions of the head 210, and particularly the dimensions of the deliver chamber 217 (and included orifices 214) are small enough that capillary forces can have a significant effect on the fluid pressures within the fluid column contained within these and larger fluid-handling parts. Particularly, each orifice 214 and connected capillary delivery chamber 217 are so dimensioned that they can be expected to fill by capillary action when the orifice 214 is brought into contact with the meniscus of a liquid to be loaded into the pulse jet. Reservoir chamber 222 is also capillary but it may be non-capillary (by non-capillary is meant that it is so dimensioned that it will not fill by capillary action after delivery chamber 217 has completely filled). While reservoir chamber 222 is capillary it is distinguishable from the delivery chamber 217. However, reservoir chamber 222 could be dimensioned such that it is indistinguishable from delivery chamber 217 (in which case the reservoir and delivery chambers may be the same chamber). A slightly negative loading pressure can simultaneously be applied to chamber 222 from pressure source 80 during a load step (described further below), which is sufficiently negative such that the fluid is drawn into the reservoir chamber 222 through the delivery chamber 217 while simultaneously being insufficient to result in ambient atmosphere entering the delivery when no further fluid is facing and adjacent the orifice (typically when a drop of liquid to be loaded, has been completely loaded). Otherwise, fluid being loaded into a jet through an orifice would be drawn into delivery chambers 217 with possible loss of prime of the jets. That is, the delivery chambers 217 should be completely filled (and preferably along with at least part of reservoir chambers 222), with a liquid face or meniscus being maintained within orifice 214 and preferably at the open end 214a of the orifices 214. Air entering orifices 214 after loading may result in loss of this condition.

Venturi 80, in the presence of a sufficient flow of anhydrous nitrogen from tank 88 and valve 86, is also capable of providing a "spotting pressure" which is slightly negative, but is typically higher (that is, less negative) than the loading pressure, during a dispensing step (described below). The spotting pressure is sufficient to retain fluid within the jets in the absence of activation of a given ejector 224. This can be obtained by processor 140 at least partially closing valve 94 from the load setting to a more restricted spotting position. The spotting pressure will typically be a known quantity for a given head 210 or can also be readily determined by experimentation. Additionally, valve 94 can be further closed from the spotting setting to a "cleaning setting" such that throat opening 89 provides in reservoir chamber 222 a holdoff pressure which is sufficiently positive to prevent liquid contacting the orifices 214 during a head cleaning step (described below) from entering delivery chambers 217 through the orifices 214. The holdoff pressure is a gas pressure in the reservoir chamber 217 (that is, there is a gas in the delivery chamber). It will also be appreciated that during a purge step for head 210 (described below), a positive "purging pressure" which is provided to reservoir chamber 222 by providing a negative pressure from pump 74 to purge station 40, could instead be replaced by providing a positive pressure to reservoir chamber 22 from throat opening 89 by at least partially closing valve 94. In this case the corresponding "purge setting" of valve 94 will typically be a further closed position from the cleaning setting since the purging pressure will typically be higher than the holdoff pressure.

The loading pressure is a negative pressure which will typically be less than the capillary pressure within a given jet during loading (for example, 10–90% of the capillary pressure), although allowances may need to be made for other factors such as the weight of the fluid column in a jet during loading (although in most fluid heads this will be negligible compared to capillary pressure). The mensiscus at an orifice 214 has a capillary pressure based on its curvature. To avoid air (or other ambient gas) from entering a delivery chamber 217 the meniscus should not move away from the end of an orifice 214. This basically implies that the value of the loading pressure should be below this capillary pressure. A suitable loading pressure for any particular apparatus can be readily determined by experimentation, simply by adjusting valve 94 (and/or valve 86 as already mentioned) until the required result is observed. That is, liquid to be loaded is drawn into reservoir chamber 222 without ambient atmosphere outside orifices 214 entering the delivery chamber 217 after the reservoir chambers have been loaded and there is no further fluid facing and adjacent the orifices 214. When too high a negative pressure is used, entry of ambient atmosphere into delivery chambers 217 can be observed directly or from the fact that the jets have lost their prime. When prime is lost, one way to regain it is to purge the head and reload it. The load setting of valve 94 can be recorded by processor 140 or can be set mechanically in valve 94. Suitable spotting, purge and holdoff pressures can also be readily determined by experimentation or calculation, and the corresponding settings of valves 84, 94 recorded by processor 140. Generally, the purging pressure is greater than the holdoff pressure which is greater than the spotting pressure, which is in turn greater than the loading pressure (that is, the spotting pressure is less negative than the loading pressure). For example, ambient pressure will typically be about 14.7 psia, the capillary pressure in a head of the above described type might be about 18 inches of water (0.65 psig), while the loading pressure might typically be about 8 inches of water below atmosphere (that is, below ambient pressure). The holdoff pressure is greater than the capillary pressure, typically about 2 to 3 times the capillary pressure (for example, about 2 psig or 55 inches of water above atmosphere), while the spotting pressure is typically about 10–90% of the capillary pressure (for example, about 5 inches of water, or 0.18 psig, below atmosphere). The purging pressure will typically be many times the capillary pressure, for example about 10 to 12 psig or 275–330 inches of water above atmosphere. Description of the pressure adjustments is also provided in U.S. Patent Application entitled "FABRICATING BIOPOLYMER ARRAYS", by M. Caren et al., assigned to the same assignee as this application, Ser. No. 09/302,922 filed on the same date as the present application.

Figure 2:
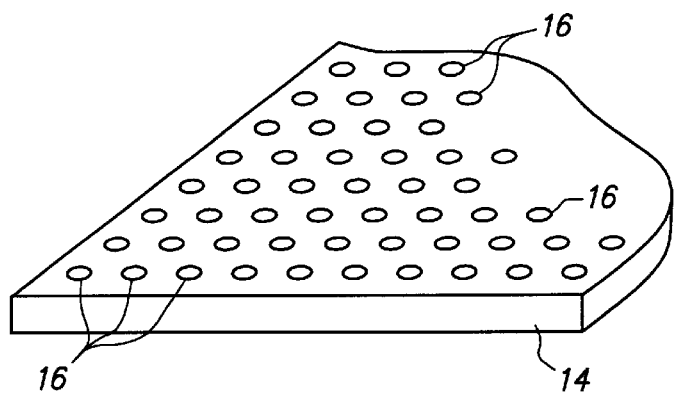
FIG. 2 is an enlarged view of a portion of FIG. 1 showing some of the identifiable individual regions of a single array of FIG. 1.
Figure 3:
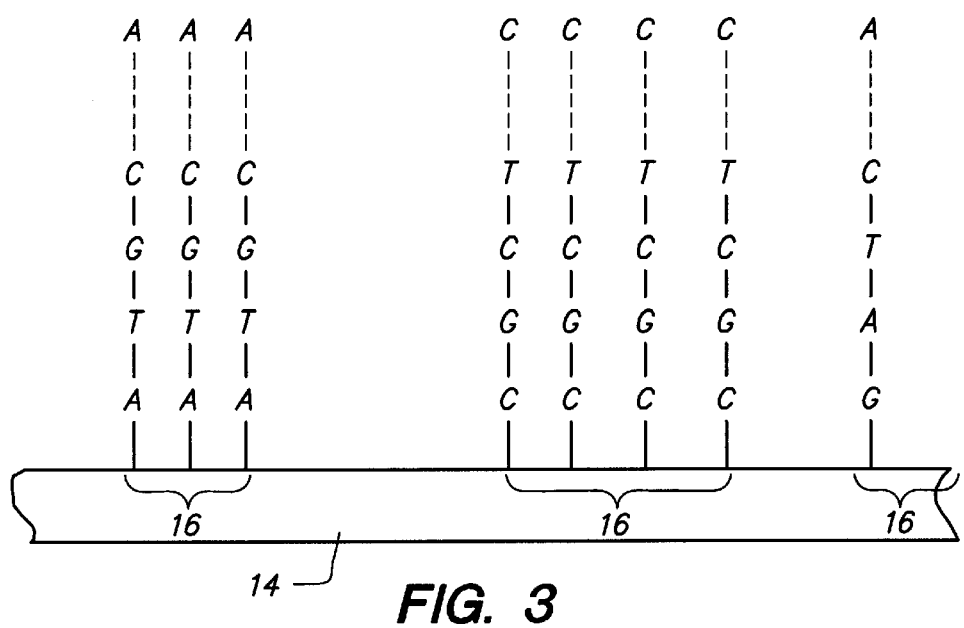
FIG. 3 is an enlarged cross-section of a portion of FIG. 2.

The apparatus of FIGS. 4 through 5 can fabricate arrays of different moieties, including arrays of different biopolymers, such as those illustrated in FIGS. 1 to 3. Operation of the apparatus to generate biopolymers will now be described although it will be understood that analogous methods can be used to generate arrays of other moieties. First, it will be assumed that tank 110 contains a suitable purging fluid (usually a buffered solution), that valve 86 has been manually opened to provide a flow of anhydrous nitrogen so that adjustment of valve 94 (and/or valve 86, as already mentioned) to the load, spotting, and cleaning settings (and optionally a purge setting) will cause the throat opening to provide the load, spotting and holdoff pressures (and optionally a purging pressure). It will also be assumed that drops of different biomonomer or biopolymer containing fluids (or other fluids) have been placed at respective notches 32 (or other drop retaining regions) of load station 30. This placement can be accomplished by manual or automated pipetting, or spotting of drops onto load station 30 using glass rods, which are of a volume required to load all of the pulse jets. Alternatively, as already mentioned, the flexible microtitre plate described in U.S. patent application "Method and Apparatus for Liquid Transfer", Ser. No. 09/183,604 could be used as load station 30. Also, pad 52 has been previously placed in cleaning station 50 and saturated with a suitable cleaning solution. Operation of the following sequences are controlled by processor 140 unless a contrary indication appears.

A loading sequence is initiated in which processor 140 directs the positioning system to position head 210 facing load station 30 with the orifices aligned, facing, and adjacent to respective drops on load station 30. As previously mentioned, during any positioning operation one axis positioning of the head 210 facing the required station can be accomplished through transporter 60, and then the other two axes positioning of head 210 can be accomplished through transporter 100. Processor 140 may optionally ensure valve 86 is open and selects the load setting of valve 94 so that the loading pressure is applied to load chamber 222 and hence to delivery chamber 217. Capillary pressure will cause fluid to then simultaneously flow in through orifices 214 to fill delivery chambers 217 and reservoir chambers 222. The load pressure assists in this filling by causing the fluid to flow faster. At this point, or shortly thereafter, there will be no further fluid facing and adjacent orifices 214, either because the fluid at load station 30 is exhausted or head 210 is moved away from load station 30. In the case where head 210 is moved away before all fluid is exhausted, some fluid may remain on the front face of head 210 and will continue to be drawn in until exhausted. In any event, because of the value of the loading pressure as discussed above, ambient atmosphere (air or nitrogen, for example) does not then enter delivery chambers 217.

A dispensing sequence is then initiated in which processor 140 then causes the positioning system to position head 210 facing substrate station 20, and particularly the mounted substrate 10, and with head 210 at an appropriate distance from substrate 10. The load setting of valve 94 is selected. Processor 140 then activates ejectors 224 in a controlled sequence while causing the positioning system to scan head 210 across substrate 10 line by line (or in some other desired pattern), to dispense droplets in a configuration which results in multiple arrays of the desired configuration on substrate 10. If necessary or desired, processor 140 can repeat the load and dispensing sequences one or more times.

Following a dispensing sequence, a purging sequence is initiated by processor 140 causing the positioning system to position head 210 facing, and in sealing engagement against, purge station such that orifices 214 are in communication with vacuum source 74. Processor 140 selects a neutral position of valves 84, 94 in which reservoir chamber 222 is essentially open to ambient pressure, and opens valve 114 such that a predetermined quantity of a purge fluid fills chambers 222, 217. Valve 114 is then closed and valve 70 opened by processor 140, so that vacuum is thereby applied from outside of orifices 214 resulting in purging of liquid in head 210 simultaneously out through orifices 214. After a suitable predetermined time has elapsed to allow complete purging of head 210, processor 140 causes the positioning system to position head 210 at cleaning station 50, ensures valve 84 is closed selects the holdoff setting of valve 94, and causes head 210 to wipe across saturated pad 52 thereby cleaning plate 212 including the regions around the orifices 214. During such operation, since the gas pressure inside delivery chamber 217 exceeds the capillary pressure, some outgassing will occur through orifices 214 (that is, bubbling of gas exiting orifices will be seen there).

The above sequences can be repeated as often as desired for a single substrate 10 or multiple different substrates (which may be manually or automatically mounted and held on substrate station 20).

Where the ejectors are electrically resistive heating elements, activation results in raising the temperature of the heater to a temperature sufficient to vaporize a small portion of the fluid immediately adjacent the heater and produce a bubble. The temperature of the heater is raised to a temperature at least about 100° C., usually at least about 400° and more usually at least about 700° C., and the temperature may be raised as high as 1000° C. or higher, but is usually raised to a temperature that does not exceed about 2000° C. and more usually does not exceed about 1500° C. Accordingly, a sufficient amount of energy will be delivered to the resistive element to produce the requisite temperature rise, where the amount of energy is generally in the range about 1.0 to 100 $\mu$J, usually about 1.5 to 15 $\mu$J. The portion of fluid in the firing chamber that is vaporized will be sufficient to produce a bubble in the firing chamber of sufficient volume to force an amount of liquid out of the orifice.

The formation of the bubble in the firing chamber traps a portion or volume of the fluid present in the firing chamber between the heating element and the orifice and forces an amount or volume of fluid out of the orifice at high speed. The amount or volume of fluid that is forced out of the firing chamber can be controlled according to the quantity of biological material to be deposited at the particular location on the receiving surface. As is well known in the ink jet print art, the amount of fluid that is expelled in a single activation event can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

Upon actuation of an ejector, as described above, fluid is expelled from the orifice and travels to the substrate surface, where it forms a spot on the substrate surface. In this manner, the biological material (such as a nucleic acid) is deposited on the substrate surface. As mentioned above, by varying the operating parameters of the apparatus, the spot dimensions can be controlled such that spots of various sizes can be produced. The sizes of the spots (and, hence, of the array features) can have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

Where a pattern of arrays is desired, any of a variety of geometries may be constructed, including for example, organized rows and columns of spots (for example, a grid of spots, across the substrate surface), a series of curvilinear rows across the substrate surface (for example, a series of concentric circles or semi-circles of spots), and the like. An array according to the invention generally includes at least tens of features, usually at least hundreds, more usually thousands, and as many as a hundred thousand or more features. Where a pattern of spots of an array is deposited on a substrate surface, the pattern may vary as desired. As such, the pattern may be in the form of organized rows and columns of spots (for example, a grid of spots, across the substrate surface), a series of curvilinear rows across the substrate surface (for example, a series of concentric circles or semi-circles of spots), and the like.

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), It will be appreciated from the above description that the apparatus and method, by including a venturi 80, provides a simple way of providing negative or positive backpressure in a pulse type fluid dispensing head while conveniently isolating sensitive reagents to contaminants (such as moisture). It will also be appreciated that variations and modifications of the above described embodiments of the invention are, of course, possible. Accordingly, the present invention is not limited to such embodiments.

What is claimed is:

1. A method of fabricating an array of biopolymers on a substrate using a biopolymer or biomonomer fluid, and using a fluid dispensing head having:
   at least one jet which can dispense droplets onto a substrate, the jet including a chamber with an orifice, and including an ejector which, when activated, causes a droplet to be ejected from the orifice;
   the method comprising:
   (a) positioning the head with the orifice facing the substrate;
   (b) dispensing multiple droplets of the biopolymer or biomonomer fluid from the head so as to form an array of droplets on the substrate;
   (c) directing a gas flow through a venturi which has a throat opening communicating with the dispensing head chamber;
   (d) varying gas flow resistance on an outlet side of the venturi, to alter the chamber pressure.

2. A method according to claim 1 wherein gas flow resistance on the venturi outlet side is adjusted to alter the chamber pressure before or after step (b).

3. A method according to claim 1 wherein a negative spotting pressure is provided from the venturi throat opening to the head chamber during dispensing of the droplets, and wherein the gas flow resistance of the venturi outlet side is adjusted to provide a positive chamber pressure.

4. A method according to claim 1 additionally comprising loading the chamber with fluid from a direction behind the orifice and wherein, following loading, the gas flow resistance of the venturi outlet side is increased to provide a positive priming pressure to the chamber so as to assist in priming the at least one jet.

5. A method according to claim 1 wherein the gas flow resistance of the venturi outlet side is increased to provide a positive purging pressure to the chamber so as to purge any fluid remaining in the chamber through the orifice.

6. A method according to claim 3 additionally comprising adding a purge fluid to the chamber prior to providing the purging pressure to the chamber.

7. A method according to claim 1 wherein the gas directed through the venturi is an anhydrous compressed gas.

8. A method according to claim 1 wherein each fluid droplet has a volume of from 0.1 to 1000 pL.

9. A method according to claim 1 additionally comprising altering the gas flow rate through the venturi by adjusting a valve on an inlet side of the venturi.

10. A method according to claim 1 additionally comprising:
    providing a spotting pressure in the chamber from the venturi throat opening while the head is facing the substrate so as to retain fluid in the chamber in the absence of the ejector being activated;
    and wherein the venturi outlet side gas flow resistance is increased to provide a purging pressure which is greater than the spotting pressure and sufficiently positive so as to purge fluid remaining in the chamber through the orifice.

11. A method according to claim 10 additionally comprising adding a purge fluid to the head prior to providing the purging pressure to the head.

12. A method according to claim 1 additionally comprising, prior to step (a):
    positioning the head facing a load station spaced from the substrate, with the orifice adjacent and facing the biomonomer or biopolymer fluid, and
    providing a loading pressure in the chamber from the venturi throat opening while the head is facing the load station, which is sufficiently negative such that the fluid is drawn into the chamber through the orifice;
    and wherein the gas flow rate through the venturi is adjusted to provide a spotting pressure while dispensing droplets from the head, which spotting pressure is higher than the loading pressure.

13. A method according to claim 12 wherein the gas flow rate is adjusted to provide the spotting pressure by adjusting a valve on an inlet side of the venturi.

14. A method according to claim 1 additionally comprising:
    positioning the head facing a load station with the orifice adjacent and facing the biomonomer or biopolymer fluid;
    providing a loading pressure in the chamber from the venturi throat opening while the head is facing the load station, which is sufficiently negative such that the fluid is drawn into the chamber through the orifice;
    positioning the head facing a purge station which is spaced from the substrate;
    and wherein:
    the gas flow rate through the venturi is adjusted by adjusting a valve on an inlet side of the venturi to provide a spotting pressure while dispensing droplets from the head, which spotting pressure is higher than the loading pressure; and following dispensing of droplets, the venturi outlet side gas flow resistance is increased to provide a purging pressure in the chamber while the head is facing the purge station which is sufficiently positive such that fluid in the chamber is purged through the orifice.

15. A method of fabricating an array of biopolymers on a substrate using a biopolymer or biomonomer fluid, and using a fluid dispensing head having:

at least one jet which can dispense droplets onto a substrate, the jet including a chamber with an orifice, and including an ejector which, when activated, causes a droplet to be ejected from the orifice;

the method comprising:

(a) positioning the head with the orifice facing the substrate;

(b) dispensing multiple droplets of the biopolymer or biomonomer fluid from the head so as to form an array of droplets on the substrate;

(c) directing a flow of anhydrous gas through a venturi which has a throat opening communicating with the dispensing head chamber.

16. A method according to claim 15 additionally comprising providing a spotting pressure in the chamber from the venturi throat opening while the head is facing the substrate so as to retain fluid in the chamber in the absence of the ejector being activated.

17. A method according to claim 15 additionally comprising:

positioning the head facing a purge station which is spaced from the substrate; and providing a purging pressure in the chamber from the venturi throat opening so as to purge fluid remaining in the chamber through the orifice.

18. A method according to claim 15 additionally comprising, prior to step (a):

positioning the head facing a load station which is spaced from the substrate, with the orifice adjacent and facing the biomonomer or biopolymer fluid, and providing a loading pressure in the chamber from the venturi throat opening while the head is facing the load station, which is sufficiently negative such that the fluid is drawn into the chamber through the orifice.

19. A method according to claim 15 wherein the head has multiple pulse jets with orifices on a common front face of the head.

20. A method according to claim 18 wherein fluid is simultaneously drawn in through the orifice of the multiple jets when the head is facing the loading station.

* * * * *